United States Patent
Hwang et al.

(10) Patent No.: US 10,057,765 B2
(45) Date of Patent: Aug. 21, 2018

(54) MASTER NODE AND OPERATION METHOD OF THE MASTER NODE

(71) Applicant: SAMSUNG ELECTRONICS CO., LTD., Suwon-si (KR)

(72) Inventors: Hyosun Hwang, Seoul (KR); Misuk Huh, Suwon-si (KR); Sang Joon Kim, Hwaseong-si (KR); Jongwook Lee, Seongnam-si (KR)

(73) Assignee: Samsung Electronics Co., Ltd., Suwon-si (KR)

(*) Notice: Subject to any disclaimer, the term of this patent is extended or adjusted under 35 U.S.C. 154(b) by 284 days.

(21) Appl. No.: 14/840,229

(22) Filed: Aug. 31, 2015

(65) Prior Publication Data
US 2016/0073256 A1    Mar. 10, 2016

(30) Foreign Application Priority Data

Sep. 4, 2014   (KR) ................ 10-2014-0117391
Feb. 4, 2015   (KR) ................ 10-2015-0017322

(51) Int. Cl.
*H04W 4/00*        (2018.01)
*H04W 12/04*       (2009.01)
*H04W 12/06*       (2009.01)
*H04W 72/12*       (2009.01)
*H04W 28/26*       (2009.01)
(Continued)

(52) U.S. Cl.
CPC .......... *H04W 12/04* (2013.01); *H04W 12/06* (2013.01); *H04W 72/1289* (2013.01); *A61B 5/0024* (2013.01); *H04W 28/26* (2013.01); *H04W 84/20* (2013.01)

(58) Field of Classification Search
CPC ......... H04L 9/08; H04L 63/061; H04L 63/08; H04L 63/12; H04W 12/04; H04W 12/06
See application file for complete search history.

(56) References Cited

U.S. PATENT DOCUMENTS

2007/0251835 A1* 11/2007 Mehta ................ A61B 5/14532
                                                       205/783
2009/0222659 A1*  9/2009 Miyabayashi ...... H04L 63/0823
                                                       713/156
(Continued)

FOREIGN PATENT DOCUMENTS

JP      2005-64984 A    3/2005
JP      2006-140743 A   6/2006
(Continued)

OTHER PUBLICATIONS

Lee, Y. et al., "Enhanced Diffie-Hellman Key Distribution using Mobile-phone," Korea Institute of Information and Communication Engineering, vol. 13 No. 12, 2009 (pp. 2563-2568).

*Primary Examiner* — Kevin C Harper
(74) *Attorney, Agent, or Firm* — NSIP Law

(57) ABSTRACT

An operation method of a master node, the method including transmitting, to a slave node, a first resource reservation information including packet information about a packet to be transferred between the master node and the slave node; allocating a radio resource corresponding to the first resource reservation information, for exchanging security information; transferring the packet using the allocated radio resource; and determining whether the packet was successfully transferred based on the packet information.

18 Claims, 7 Drawing Sheets

(51) Int. Cl.
*H04W 84/20* (2009.01)
*A61B 5/00* (2006.01)

(56) References Cited

U.S. PATENT DOCUMENTS

| | | | |
|---|---|---|---|
| 2009/0228707 A1* | 9/2009 | Linsky | G06F 21/31 |
| | | | 713/171 |
| 2010/0002721 A1* | 1/2010 | Eller | H04L 67/14 |
| | | | 370/466 |
| 2010/0042841 A1 | 2/2010 | King et al. | |
| 2011/0217950 A1 | 9/2011 | Kozlay | |
| 2012/0063598 A1 | 3/2012 | Huh | |
| 2013/0343542 A1 | 12/2013 | Rosati et al. | |
| 2015/0281874 A1* | 10/2015 | Cheng | H04B 15/00 |
| | | | 455/41.1 |

FOREIGN PATENT DOCUMENTS

| | | |
|---|---|---|
| JP | 2006-332903 A | 12/2006 |
| JP | 2009-303188 A | 12/2009 |

\* cited by examiner

MASTER NODE AND OPERATION METHOD OF THE MASTER NODE

CROSS-REFERENCE TO RELATED APPLICATION(S)

This application claims the benefit under 35 USC 119(a) of Korean Patent Application No. 10-2014-0117391, filed on Sep. 4, 2014, and Korean Patent Application No. 10-2015-0017322, filed on Feb. 4, 2015, in the Korean Intellectual Property Office, the entire disclosures of which are incorporated herein by reference for all purposes.

BACKGROUND

1. Field

The following description relates to a master node and an operation method of the master node.

2. Description of Related Art

A user needs to prevent information from being externally exposed when exchanging information through wireless communication. A security function may be provided to the user to prevent information from being externally exposed. For example, an integrity check or an encryption may be provided. An encryption key is to be shared between devices to apply the security function.

Although the security function is applied when exchanging information between devices, a third party may acquire information. Here, acquirement of information by the third party is a man in the middle (MITM) attack.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

In a general aspect, there is provided a master node including a scheduler configured to transmit, to a slave node, a first resource reservation information including packet information about a packet to be transferred between the master node and the slave node, and to allocate a radio resource corresponding to the first resource reservation information, for exchanging security information; an exchanger configured to transfer the packet using the allocated radio resource; and a controller configured to determine whether the packet was successfully communicated based on the packet information.

The scheduler may transmit a second resource reservation information to the slave node in response to of the controller having determined that the packet was not successfully transferred, and allocate a radio resource corresponding to the second resource reservation information.

The scheduler may transmit second resource reservation information to the slave node, to transmit master node key information to the slave node based on the second resource reservation information, and may allocate a first radio resource used to receive slave node key information.

The master node key information may include either one or both of a public key and a random value corresponding to the master node, and the slave node key information may include either one or both of a public key and a random value corresponding to the slave node.

The controller may determine whether either one or both of the master node key information and the slave node key information has been lost.

The scheduler may transmit third resource information to the slave node in response to the controller determining that the master node key information and the slave node key information were successfully transferred, may transmit master node authentication information based on the third resource reservation information, and may allocate a second radio resource used to receive slave node authentication information.

The master node authentication information may be generated at the master node based on the master node key information and the slave node key information, and the slave node authentication information may be generated at the slave node based on the master node key information and the slave node key information.

The controller may be configured to determine whether the master node authentication information and the slave node authentication information has been lost.

The master node key information and the slave node key information may be included in a first packet group, and the master node authentication information and the slave node authentication information included in a second packet group, and the scheduler may set up a first dedicated channel for exchanging a plurality of packets included in the first packet group, and may set up a second dedicated channel for exchanging a plurality of packets included in the second packet group.

The controller may terminate a connection of the first dedicated channel in response to of the controller determining that a packet included in the first packet group has been lost.

The master node may also include a master key generator configured to generate a master key used to encrypt data transmitted and received between the master node and the slave node in response the controller having determined that the packet was successfully transferred.

In another general aspect, there is provided a master node including a scheduler associated with a link layer; and a security manager configured to transfer security information to the scheduler, with the security manager being configured to request the scheduler to allocate either one or both of a radio resource and a channel for exchanging a key with the slave node, and the link layer being configured to transmit the security information to the slave node using the allocated either one or both of the radio resource and the channel.

The scheduler may be configured to manage the radio resource for transmitting the security information.

The master node may also include a controller configured to determine a presence or an absence of an error in a packet for the key exchange and to control the scheduler to allocate another radio resource in response to the presence of the error.

The controller may be configured to cancel the packet for the key exchange in response to the presence of the error.

In another general aspect, there is provided an operation method of a master node, the method including transmitting, to a slave node, a first resource reservation information including packet information about a packet to be transferred between the master node and the slave node; allocating a radio resource corresponding to the first resource reservation information, for exchanging security information; transferring the packet using the allocated radio resource; and determining whether the packet was successfully transferred based on the packet information.

The method may also include transmitting a second resource reservation information to the slave node in response to the determining having determined that the packet was not successfully transferred, and allocating a radio resource corresponding to the second resource reservation information.

The transmitting of the first resource reservation information may include transmitting second resource reservation information to the slave node identifying a first radio resource as to be used to transmit master node key information and to receive slave node key information.

The master node key information may include either one or both of a public key and a random key corresponding to the master node, and the slave node key information may include either one or both of a public key and a random key corresponding to the slave node.

The determining may include determining whether either one or both of the master node key information and the slave node key information has been lost.

The first resource reservation information may also include transmitting third resource reservation information to the slave node identifying a second radio resource as to be used to transmit master node authentication information and to receive slave node authentication information, in response to a determination that the master node key information and the slave node key information were successfully transferred.

The master node authentication information may be generated at the master node based on the master node key information and the slave node key information, and the slave node authentication information may be generated at the slave node based on the master node key information and the slave node key information.

The determining may include determining whether the master node authentication information and the slave node authentication information has been lost.

The method may also include transmitting, to the slave node, an additional resource reservation information including additional packet information about an additional packet to be transferred between the master node and the slave node, in response of the determining having determined that the packet was successfully transferred; and allocating an additional resource corresponding to the additional resource reservation information.

Other features and aspects will be apparent from the following detailed description, the drawings, and the claims.

Figure 1A:
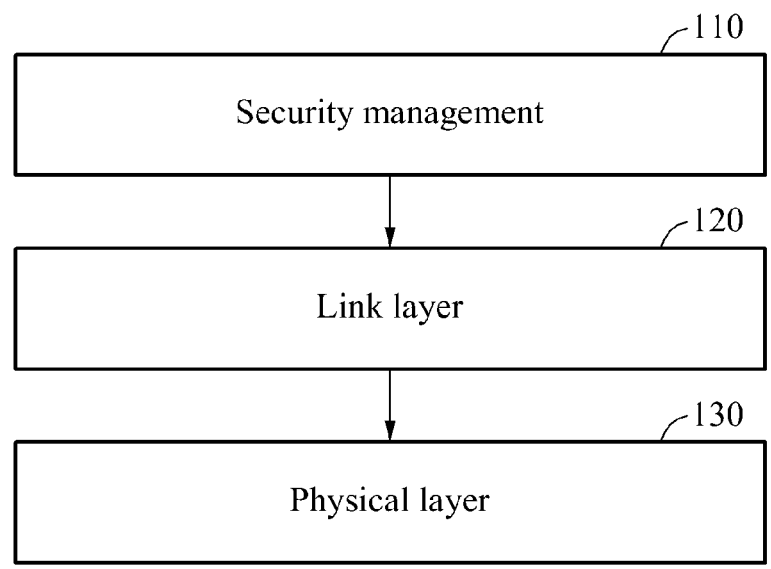
FIGS. 1A and 1B are diagrams illustrating an example of a master node allocating a resource and transmitting security information.

Throughout the drawings and the detailed description, unless otherwise described or provided, the same drawing reference numerals will be understood to refer to the same elements, features, and structures. The drawings may not be to scale, and the relative size, proportions, and depiction of elements in the drawings may be exaggerated for clarity, illustration, and convenience.

DETAILED DESCRIPTION

The following detailed description is provided to assist the reader in gaining a comprehensive understanding of the methods, apparatuses, and/or systems described herein. However, various changes, modifications, and equivalents of the methods, apparatuses and/or systems described herein will be apparent to one of ordinary skill in the art. The sequences of operations described herein are merely examples, and are not limited to those set forth herein, but may be changed as will be apparent to one of ordinary skill in the art, with the exception of operations necessarily occurring in a certain order. Also, descriptions of functions and constructions that are well known to one of ordinary skill in the art may be omitted for increased clarity and conciseness.

The features described herein may be embodied in different forms, and are not to be construed as being limited to the examples described herein. Rather, the examples described herein have been provided so that this disclosure will be thorough and complete, and will convey the full scope of the disclosure to one of ordinary skill in the art.

Various alterations and modifications may be made to the examples. Here, the examples are not construed as limited to the disclosure and should be understood to include all changes, equivalents, and replacements within the idea and the technical scope of the disclosure.

The terminology used herein is for the purpose of describing particular examples only and is not to be limiting of the examples. As used herein, the singular forms "a", "an", and "the" are intended to include the plural forms as well, unless the context clearly indicates otherwise. It will be further understood that the terms "include/comprise" and/or "have" when used in this specification, specify the presence of stated features, integers, steps, operations, elements, components, and/or combinations thereof, but do not preclude the presence or addition of one or more other features, numbers, steps, operations, elements, components, and/or groups thereof.

Unless otherwise defined, all terms including technical and scientific terms used herein have the same meaning as commonly understood by one of ordinary skill in the art to which examples belong. It will be further understood that terms, such as those defined in commonly-used dictionaries, should be interpreted as having a meaning that is consistent with their meaning in the context of the relevant art and will not be interpreted in an idealized or overly formal sense unless expressly so defined herein.

When describing the examples with reference to the accompanying drawings, like reference numerals refer to like constituent elements and a repeated description related thereto will be omitted. When it is determined detailed description related to a related known function or configuration they may make the purpose of the examples unnecessarily ambiguous in describing the examples, the detailed description will be omitted here.

Figure 1B:
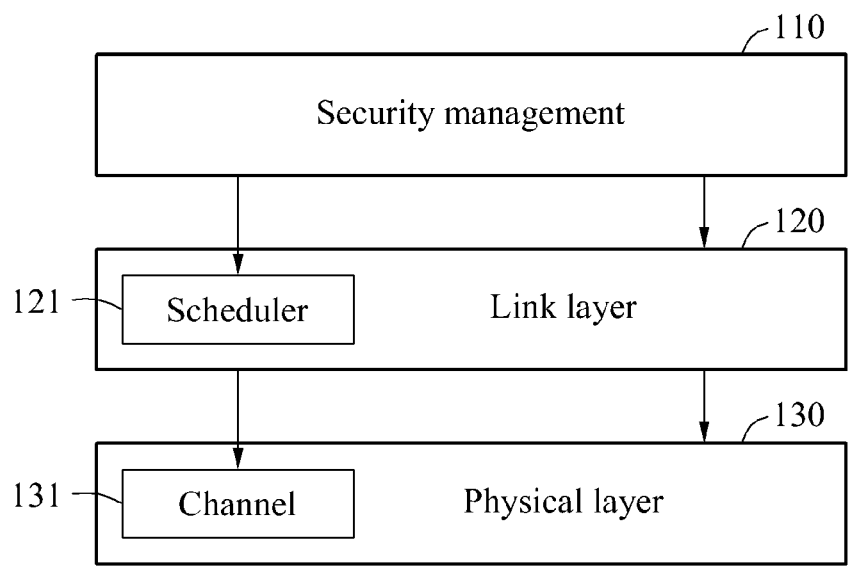

FIGS. 1A and 1B are diagrams illustrating an example of a master node allocating a resource and transmitting security information.

Referring to FIG. 1A, security management 110 is an upper layer with respect to a media access control (MAC)

layer or a link layer 120. A security manager of the security management transmits security information to the link layer 120. The link layer 120 packetizes the security information and independently transmits the packetized security information. A resource for transmitting the security information may be separately controlled or may not be allocated.

Referring to FIG. 1B, the master node includes a scheduler 121 and a security manager (not shown). The security manager of the security management 110 transfers security information to the link layer 120. The security management 110 may be associated with an upper layer of the MAC or the link layer 120.

The scheduler 121 controls or manages a radio resource for transmitting security information. For example, the security manager may request the scheduler 121 to allocate a radio resource for transmitting security information to a slave node. Also, the security manager may request the scheduler 121 to allocate a channel 131 for a key exchange. Also, the security manager may request the scheduler 121 to allocate a radio resource for the key exchange. In response to the request of the security manager, the scheduler 121 may allocate the radio resource or the channel 131.

The link layer 120 packetizes the security information and transmits the packetized security information to the slave node using the radio resource allocated for the key exchange.

Security information relates to including encryption information or encrypted information for establishing secure communication between the master node and the slave node, which will be described later. The security information may include master node key information and/or master node authentication information, which will be described later. Also, the security information may include slave node key information and/or slave node authentication information transmitted by the slave node.

A packet including a random value and a public key of the master node may be transmitted to the slave node through the radio resource allocated by the scheduler 121. Also, a packet including a random value and a public key of the slave node may be transmitted to the master node through the radio resource allocated by the scheduler 121.

The master node may further include a controller. The controller may determine whether an error is present in a packet for the key exchange. When the error is present, the controller may cancel the packet transmitted/received through the allocated radio resource. For example, the scheduler 121 may determine whether an error is present in a packet received from the slave node, and may cancel the received packet when the error is present. When the error is present, the controller may control the scheduler 121 to allocate another radio resource.

Technical matters described above with reference to FIG. 1 may be applicable to technical matters of FIGS. 2 through 7.

Figure 2:
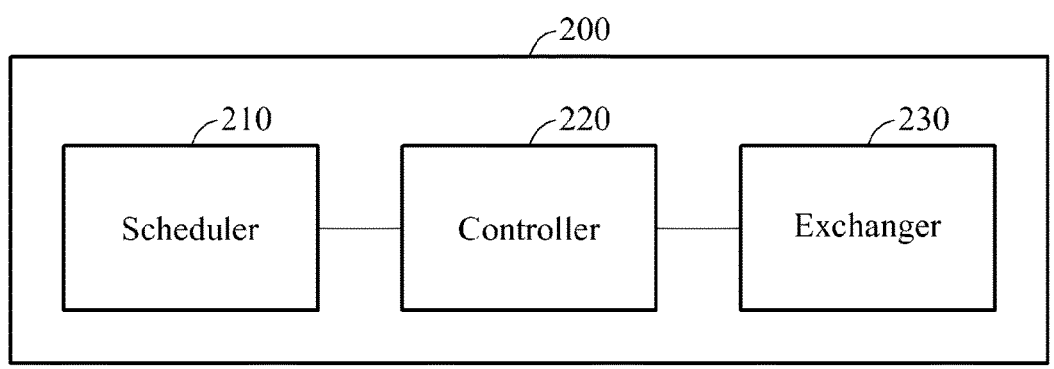
FIG. 2 is a block diagram illustrating an example of a master node.

FIG. 2 is a block diagram illustrating an example of a master node 200.

Referring to FIG. 2, the master node 200 includes a scheduler 210, a controller 220, and an exchanger 230.

The scheduler 210 transmits resource reservation information to a slave node. The resource reservation information may be used to allocate a resource between the master node 200 and the slave node. The scheduler 210 allocates a resource for exchanging security information. For example, the scheduler 210 may allocate or manage a radio resource and/or a channel so that the master node transmits security information including a public key of the master node and the like to the slave node, and receives security information including a public key of the slave node and the like.

Also, the resource reservation information may include packet information about a packet exchanged between the master node 200 and the slave node. For example, when packets A and B are to be exchanged between the master node 200 and the slave node, the master node 200 may transmit resource reservation information to the slave node that includes a number of packets to be exchanged. The master node 200 may transmit, to the slave node, information indicating that the packets A and B are packets to be exchanged.

The master node 200 and the slave node may become aware of a packet to be received or a packet to be transmitted based on packet information.

The scheduler 210 allocates a radio resource based on the resource reservation information. For example, when a communication method used between the master node 200 and the slave node is a time division multiple access (TDMA) communication method, the master node 200 may allocate a time resource. As another example, when the communication method used between the master node 200 and the slave node is a frequency division multiple access (FDMA) communication method, the master node 200 may allocate a frequency resource. In some examples, the master node 200 may allocate both a time resource and a frequency resource.

The exchanger 230 exchanges packets using the allocated radio resource. The exchange may indicate that the master node 200 transfers a packet to the slave node and transfers a packet from the slave node. For example, the master node 200 may transmit a packet A to the slave node and may receive a packet B from the slave node.

The controller 220 determines whether exchanged transferred packet is lost, based on the packet information. The master node 200 and the slave node are aware of in advance of an exchange of packets and the number of packets to be exchanged, based on the packet information. For example, when packets A and B are to be exchanged between the master node 200 and the slave node, the master node 200 and the slave node may be aware of in advance that the packets A and B are to be exchanged. That is, the master node 200 may be aware of in advance that the packet B is to be transferred from the slave node, and the slave node may be aware of in advance that the master node 200 will be transferring the packet A. Accordingly, when the packet B is not properly received by master node 200, the master node 200 may determine that the packet B has been lost, and that the transfer of packet B was not successful.

The controller 220 determines whether a predetermined packet is transferred within a packet exchange interval. In detail, the controller 220 determines whether the master node 200 has transmitted a packet to the slave node or whether the master node 200 has received a packet from the slave node, within the packet exchange interval. When the master node 200 fails to successfully receive a packet from the slave node, the controller 220 may determine that predetermined packet was not successfully transferred within the packet exchange interval. In this example, the predetermined packet indicates a packet was to be received by the master node 200 or the slave node based on packet information.

When at least one of exchanged packets is lost, the scheduler 210 again transmits resource reservation information to the slave node. In the above example, in response to the master node 200 failing to receive the packet B, the scheduler 210 may retransmit the resource reservation information previously transmitted to the slave node. Alternatively, the scheduler 200 may obtain new resource reservation information. The scheduler 210 allocates a radio resource based on the newly transmitted resource reservation information. When the radio resource is allocated, the exchanger 230 retransmits a packet transmitted before allocating the radio resource. For example, the exchanger 230 may retransmit the previously transmitted packet A to the slave node.

In an example, the scheduler 210 transmits first resource reservation information to the slave node to identify a first radio resource. In response to a transmission of the first resource reservation information, the master node 200 may determine that master node key information is to be transmitted. The master node key information may include a public key and a random value corresponding to the master node 200. Also, in response to a transmission of the first resource reservation information, the master node 200 may determine that slave node key information is to be received. The slave node key information may include a public key and a random value corresponding to the slave node.

In response to a reception of the first resource reservation information, the slave node may determine that master node key information is to be received from the master node 200. Also, in response to a reception of the first resource reservation information, the slave node may determine that slave node key information is to be transmitted to the master node 200.

The controller 220 determines whether at least one of master node key information and slave node key information is lost. For example, the controller 220 may determine whether the slave node has received the master node key information. When the slave node does not transmit an acknowledgement (ACK) to the master node 200 in response to a transfer of the master node key information to the slave node, that is, when the master node 200 does not receive the ACK, the controller 220 may determine that the master node key information is lost. Alternatively, when the master node 200 does not receive, or incorrectly receives, the slave node key information the controller 220 may determine that the master node key information is lost. Alternatively, when the master node 200 does not receive, or incorrectly receives, the slave node key information, the controller 220 may determine that the slave node key information is lost.

When at least one of the master node key information and the slave node key information is determined to have been lost, the scheduler 210 may retransmit the previously transmitted first resource reservation information. The scheduler 210 may reallocate a radio resource corresponding to the first resource reservation information.

In an example, in response to determining that master node key information and slave node key information were successfully exchanged, the master node 200 may generate master node authentication information based on the master node key information and the slave node key information. The master node authentication information is used to authenticate the master node 200 to the slave node. The slave node may generate the slave node authentication information based on the master node key information and the slave node key information.

In an example, in response to determining that master node key information and slave node key information were successfully exchanged, the scheduler 210 transmits second resource reservation information to the slave node identifying a second radio resource. In response to a transmission of the second resource reservation information, the master node 200 may determine that master node authentication information is to be transmitted. Also, in response to a transmission of the second resource reservation information, the master node 200 may determine that slave node authentication information is to be received.

In response to receiving the second resource reservation information, the slave node may determine that master node authentication information is to be transferred from the master node 200. Also, in response to receiving the second resource reservation information, the slave node may determine that slave node authentication information is to be transmitted to the master node 200.

The scheduler 210 allocates a second radio resource corresponding to the second resource reservation information. The exchanger 230 transfers master node authentication information to the slave node and transfers slave node authentication information from the slave node through the second radio resource.

The controller 220 determines whether at least one of master node authentication information and slave node authentication information is lost. For example, the controller 220 may determine whether the slave node has received the master node authentication information. When the slave node does not transmit an ACK to the master node 200 in response to a transfer of the master node authentication information to the slave node, that is, when the master node 200 does not receive the ACK, the controller 220 may determine that the master node authentication information is lost. Also, when the master node 200 does not receive, or incorrectly receives, the slave node authentication information, the controller 220 may determine that the slave node authentication information is lost.

The master node 200 authenticates the slave node based on the master node authentication information and the slave node authentication information. Also, the slave node authenticates the master node 200 based on the master node authentication information and the slave node authentication information.

When the authentication is completed, the master node 200 and the slave node generate a master key used to transmit and receive data securely using encryption. For example, the master node 200 and the slave node may generate a master key for securely transmitting and receiving biosignals, financial information, or personal information. The master node 200 and the slave node may encrypt such information using the master key for encryption.

In an example, the master node 200 may classify, into a first packet group and a second packet group, a plurality of packets transmitted to and received from the slave node. The first packet group may include the aforementioned master node key information and slave node key information, and the second packet group may include the aforementioned master node authentication information and slave node authentication information.

The scheduler 210 may set up a first dedicated channel for exchanging a plurality of packets included in the first packet group. The master node 200 may transfer the plurality of packets included in the first packet group through the first dedicated channel only. Transfer of the plurality of packets included in the first packet group may be performed through a limited radio resource only.

In response to determining that at least one of the plurality of packets included in the first packet group was not successfully transferred, the controller 220 terminates a connection of the first dedicated channel. When the connection of the first dedicated channel is terminated, the scheduler 210 resets the first dedicated channel for exchanging again the plurality of packets included in the first packet group.

The scheduler 210 may set up a second dedicated channel for exchanging a plurality of packets included in the second packet group, based on the exchange of the plurality of packets included in the first packet group. Transfer of the plurality of packets included in the second packet group may be performed through a limited radio resource only.

In response to determining that at least one of the plurality of packets included in the second packet group was not successfully transferred, the controller 220 terminates a connection of the second dedicated channel. When the connection of the second dedicated channel is terminated, the scheduler 210 resets up the second dedicated channel for exchanging again the plurality of packets included in the second packet group.

In the event that the number of reset-ups of the first dedicated channel or the second dedicated channel is greater than or equal to a threshold, the master node 200 may provide a user with a message such as "cannot connect to the slave node". Alternatively, when the number of retransmissions of the plurality of packets included in the first packet group or the second packet group is greater than or equal to a threshold, the master node 200 may provide the user with a message such as "cannot connect to the slave node".

Figure 3:
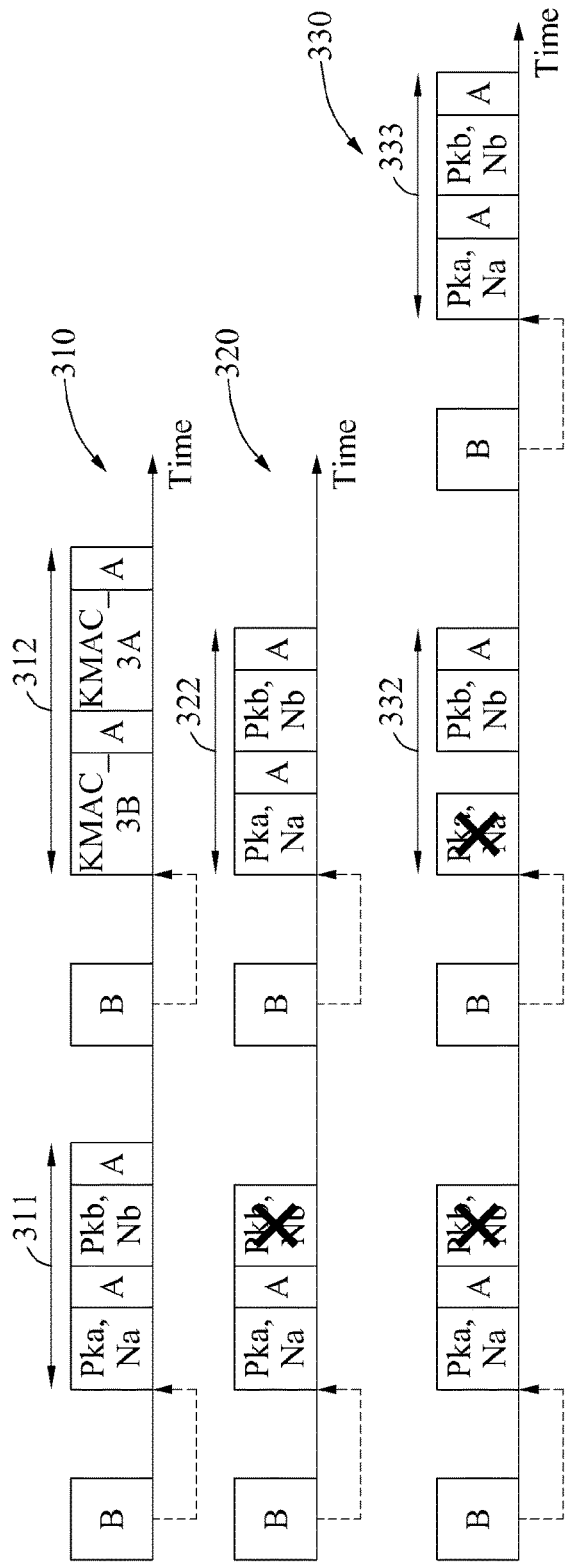
FIG. 3 is a diagram illustrating an example of a master node allocating a resource.

FIG. 3 is a diagram illustrating an example of a master node allocating a resource.

Referring to FIG. 3, a time resource is allocated to transmit and receive a packet. An example of allocating a time resource is only an example and, as previously discussed, a frequency resource may be allocated to transmit and receive a packet. Further, a time resource and a frequency resource may both be allocated.

The master node may identify a radio resource for packet transmission through a beacon based on a type of a network. Alternatively, the master node may identify a radio resource for packet transmission based on a request to send/clear to send control (rts/cts) frame. The beacon or the rts/cts frame may correspond to an example in which the master node transmits a resource reservation message for resource allocation. The resource reservation message, and how it is transmitted, may vary based on a type of a network to which the master node belongs.

In a first example 310, the master node exchanges key information and a random value with a slave node during a first time period 311. The first time period 311 is based on a radio resource allocated by the master node. The master node transfers, to the slave node, a packet including a public key and a random value (Pka and Na) of the master node. In response thereto, the slave node transmits an ACK to the master node. The master node transfers, from the slave node, a packet including a public key and a random value (Pkb and Nb) of the slave node. In response thereto, the master node transmits an ACK to the slave node. The public keys, Pka and Pkb, and the random values, Na and Nb, may be exchanged only during the first time period 311.

When a public key and random value exchange process during the first time period 311 is complete, each of the master node and the slave node may generate corresponding authentication information. For example, each of the master node and the slave node may generate corresponding authentication information based on a pre-stored Diffie-Hellman key and a predetermined algorithm.

The master node generates master node authentication information for use by the slave node, and allocates a radio resource to receive slave node authentication information from the slave node. The master node may transmit a resource reservation message to identify the radio resource, such as beacon B illustrated before time period 311.

After transmitting the resource reservation message, the master node allocates the radio resource. In response to an allocation of the radio resource, a second time period 312 may be set up to transmit and receive authentication information. During the second time period 312, the master node transfers master node authentication information to the slave node and the transfers slave node authentication information from the slave node.

The master node transfers slave node authentication information (KMAC_3B) from the slave node. In response thereto, the master node transmits an ACK. The master node transfers master node authentication information KMAC_3A to the slave node. In response thereto, the slave node transmits an ACK to the master node.

Thus, in the first example 310, the master node and the slave node exchange information for establishing encrypted communication during the first time period 311 and the second time period 312. Based on the exchanged information, the master node may generate a master key together with the slave node.

In contrast to the first example 310, in a second example 320, an ACK to be transmitted after a packet including Pkb and Nb during a first time period is not transmitted by the master node in response to not successfully transferring the packet including Pkb and Nb from the slave node. In response to failing to receive the packet including Pkb and Nb, the master node determines that the packet including Pkb and Nb was not successfully transferred.

Based on the determination that the transfer was unsuccessful, the master node may reallocate the radio resource. The information including Pka, Na, Pkb, and Nb may be exchanged during a reset-up time period 322.

In a third example 330, an ACK to be transmitted after a packet including Pkb and Nb during a first time period is not transmitted by the master node in response to not successfully transferring the packet including Pkb and Nb from the slave node. In response to not receiving the packet including Pkb and Nb, the master node determines that the packet including Pkb and Nb was not successfully transferred.

The master node may reallocate the radio resource. The master node and the slave node may attempt to exchange information including Pka, Na, Pkb, and Nb during a first reset-up time period 332. As illustrated in the third example 330, during the first reset-up time period 332, an ACK to be transmitted by the slave node after the slave node receives the packet including Pka and Na is not received by the master node. In response to failing in receiving the ACK, the master node determines that the packet including Pka and Na was not successfully transferred.

Based on the determination that the packet was not successfully transferred, the master node may reallocate the radio resource to exchange information including Pka, Na, Pkb, and Nb during a second reset-up time period 333. The master node may reallocate the radio resource and attempt additional reset-up time periods until information including Pka, Na, Pkb, and Nb is successfully exchanged.

In an example, when a number of allocations of a radio resource is greater than or equal to a threshold, the master node may provide a user with a message indicating that an ongoing procedure is terminated. The ongoing procedure may be a procedure for exchanging information such as key information or authentication information.

Figure 4:
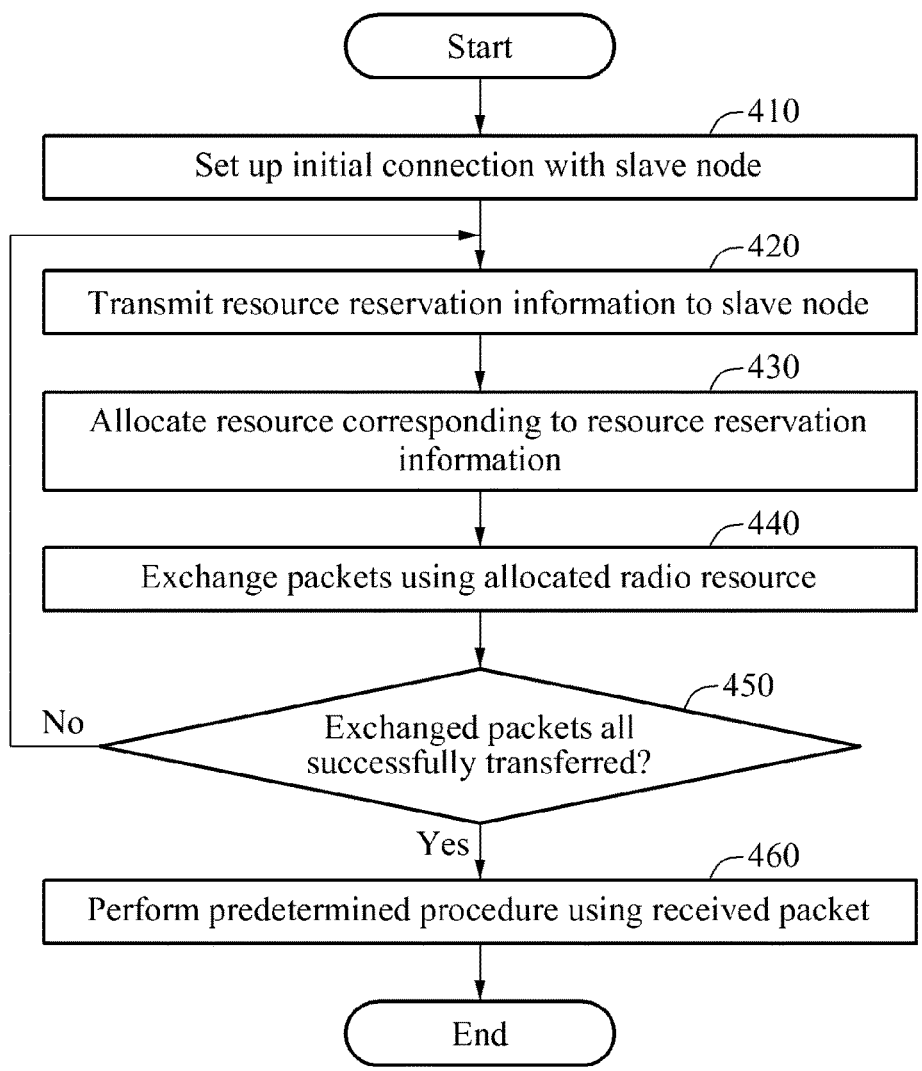
FIG. 4 is a flowchart illustrating an example of an operation method of a master node.

FIG. 4 is a flowchart illustrating an example of an operation method of a master node.

Referring to FIG. 4, in operation 410, the master node sets up an initial connection with a slave node. For example, the initial connection may be a near field wireless connection. Based on a setup of the initial connection, the master node may receive identification information of the slave node from the slave node. The identification information may be an ID or a MAC address of the slave node. The master node may generate an authentication ID of the slave node based on the identification information. The authentication ID may be already known to the user. The master node may output the authentication ID. For example, the master node may display an authentication ID of the slave node on a display of the master node, which may be used by a user to compare the displayed authentication ID with known information for the slave node. The initial authentication of the slave node may succeed or fail based on a comparison result.

In operation 420, the master node transmits resource reservation information to the slave node. Here, the resource reservation information may include packet information about packets exchanged between the master node and the slave node.

In operation 430, the master node allocates a radio resource corresponding to the resource reservation information, for exchanging security information. In some examples, operation 430 may occur before operation 420. In operation 440, the master node exchanges the packets with the slave node using the allocated radio resource. In operation 450, the master node determines whether all of the exchanged packets were successfully transferred. In the event that a packet is determined to have been lost, the master node may retransmit the previously transmitted resource reservation information.

On the other hand, in the event that all of the packets are determined to have been transferred successfully, in operation 460 the master node performs a predetermined procedure using a packet received from the slave node. For example, the master node may transmit additional resource reservation information to the slave node. Here, the additional resource reservation information may include additional packet information about additional packets exchanged between the master node and the slave node. The master node may allocate an additional resource corresponding to the additional resource reservation information.

In an example, the master node may transmit first resource reservation information to the slave node to identify a first radio resource used to transfer master node key information to the slave node and to transfer slave node key information from the slave node. Here, the master node key information may include at least one of a public key and a random value corresponding to the master node. The slave node key information may include at least one of a public key and a random value corresponding to the slave node.

The master node may, for example, allocate the first radio resource based on the first resource reservation information. The master node may transmit the master node key information to the slave node using the first radio resource. In response to receiving the master node key information, the slave node may transmit an ACK to the master node. The slave node may transmit the slave node key information to the master node using the first radio resource. In response to receiving the slave node key information, the master node may transmit an ACK to the slave node.

The master node may determine whether at least one of the master node key information and the slave node key information was not successfully transferred. For example, when at least one of the transmitted ACK and the received ACK is absent, the master node may determine that at least one of the master node key information and the slave node key information was not successfully transferred or was lost.

When none of the transmitted ACK and the received ACK is lost, the master node may generate master node authentication information using a public key included in the slave node key information and a unique key. The slave node may generate slave node authentication information using a public key included in the master node key information and a unique key.

In an example, the master node may transmit second resource reservation information to the slave node in response to a determination that the master node key information and the slave node key information were successfully exchanged. A second radio resource corresponding to the second resource reservation information may be allocated and used to transmit the master node authentication information and to receive the slave node authentication information.

The master node may transmit master node authentication information to the slave node using the second radio resource. In response to receiving the master node authentication information, the slave node may transmit an ACK to the master node. The slave node may transmit the slave node authentication information to the master node using the second radio resource. In response to receiving the slave node authentication information, the master node may transmit an ACK to the slave node.

The master node may determine whether at least one of the master node authentication information and the slave node authentication information was not successfully transferred. For example, when at least one of the transmitted ACK and the received ACK is absent, the master node may determine that at least one of the master node authentication information and the slave node authentication information was not successfully transferred or was lost.

Technical matters made above with reference to FIGS. 1 through 3 may be applicable to technical matters of FIG. 4 and thus, further descriptions will be omitted.

Figure 5:
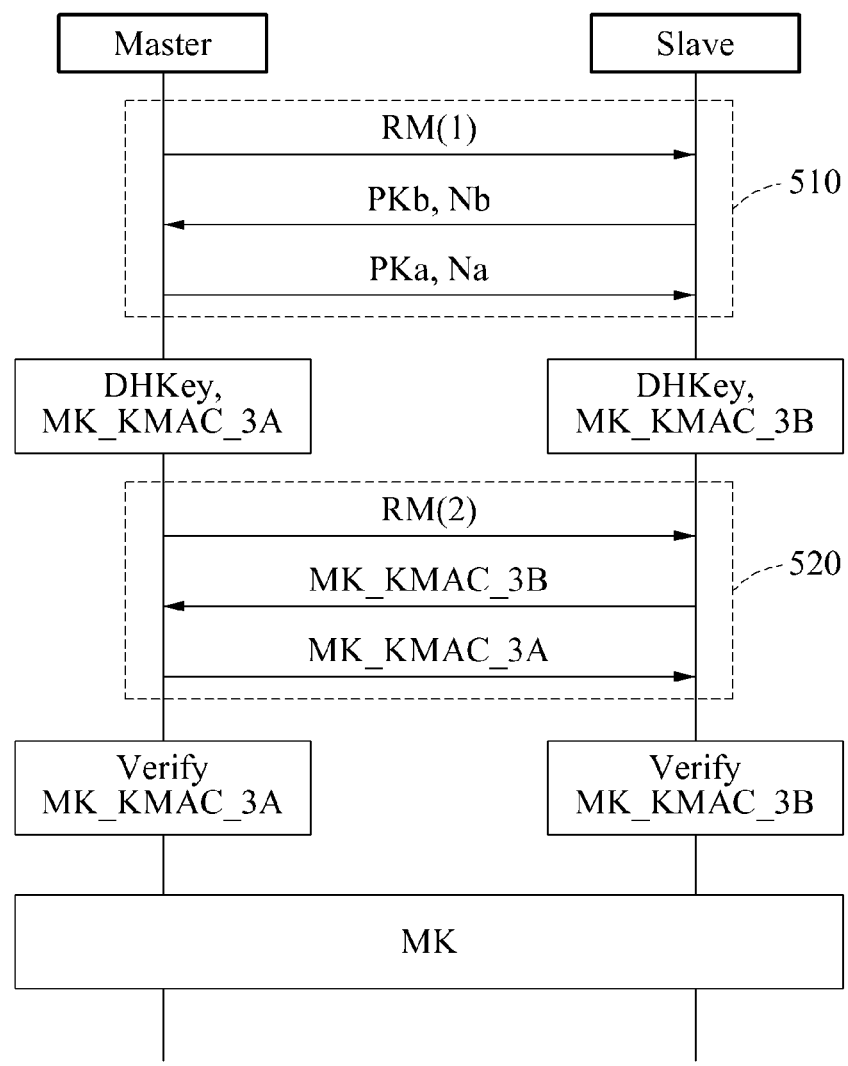
FIG. 5 is a diagram illustrating an example of an operation between a master node and a slave node.

FIG. 5 is a diagram illustrating an example of an operation between a master node and a slave node.

Referring to FIG. 5, in operation 510, the master node transmits resource management message RM(1) to the slave node. A transmission of RM(1) may indicate that the master node controls a resource for transferring information between the master node and the slave node. The master node may allocate a radio resource or may set up a channel corresponding to a resource identified in RM(1). Using the allocated resource, the master node transfer a public key and a random value (Pkb and Nb) of the slave node from the slave node. Also, the master node transfers a public key and a random value (Pka and Na) of the master node to the slave node. Pka and Na, and Pkb and Nb may be transferred by being transmitted or received using a radio resource or a channel corresponding to a resource identified in RM(1). In operation 510, the allocated radio resource or the allocated channel is a radio resource or a channel dedicated for exchanging Pka and Na and Pkb and Nb.

The master node determines whether Pkb and Nb are successfully transferred from the slave node. Also, the master node determined whether Pka and Na are successfully transferred to the slave node. When the master node has Pkb and Nb and the slave node has Pka and Na, each of the master node and the slave node may generate corresponding authentication information based on a pre-stored Diffie-Hellman key (DHkey) and a predetermined algorithm.

In operation 520, the master node transmits resource management message RM(2). A transmission of RM(2) may indicate that the master node controls a resource for transferring information between the master node and the slave node. The master node may allocate a radio resource or may set up a channel corresponding to a resource identified in RM(2). Using the allocated resource, the master node transfers slave node authentication information from the slave node. Also, the master node transfers master node authentication information to the slave node. Each of the master node authentication information and the slave node authentication information may be transferred using a radio resource or a channel corresponding to a resource identified in RM(2). In operation 520, the allocated radio resource or the allocated channel may be a radio resource or a channel dedicated for exchanging master node authentication information and slave node exchange information.

The master node authenticates the slave node by exchanging authentication information. Also, the slave node authenticates the master node by exchanging authentication information. After authenticating the master node and the slave node, the master node and the slave node generate a master key (MK) used to encrypt data.

Figure 6:
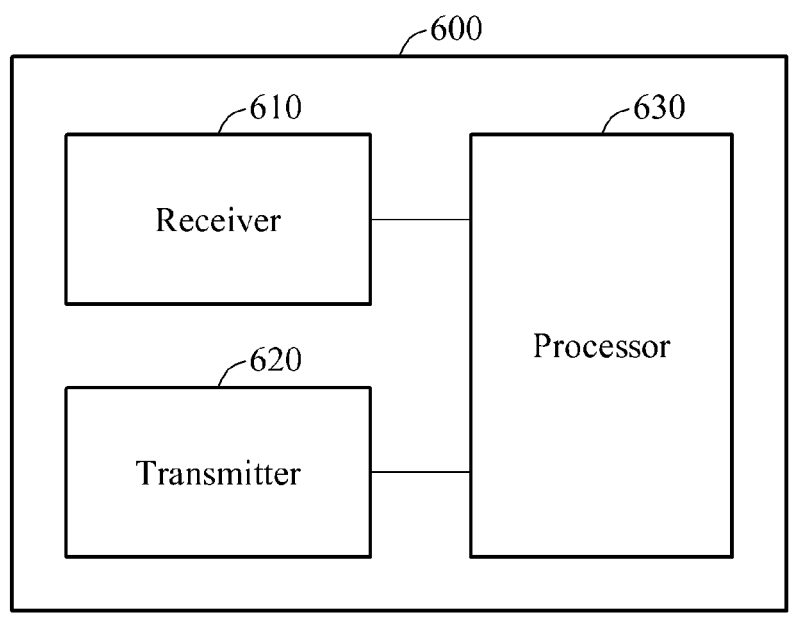
FIG. 6 is a diagram illustrating an example of a slave node.

FIG. 6 is a diagram illustrating an example of a slave node 600.

Referring to FIG. 6, the slave node 600 includes a receiver 610, a transmitter 620, and a processor 630.

The receiver 610 is configured to receive packets transmitted from a master node through a radio resource or channel set up between the master node and the slave node 600. For example, the receiver 610 may receive a packet including a public key and a random value of the master node transmitted from the master node.

The transmitter 620 is configured to transmit packets to the master node through a radio resource or channel set up between the master node and the slave node 600. For example, the transmitter 620 may transmit a packet including a public key and a random value of the slave node to the master node.

The master node may determine whether the slave node 600 has received a packet including the public key and the random value of the master node. In the event the master node determines the packet has been lost, the master node may terminate a connection with the slave node and may reset up the radio resource or channel.

On the other hand, when no packet is lost, the processor 630 generates slave node authentication information using the public key and the random value of the master node. Also, when no packet is lost, the master node may set up a radio resource or channel different from the previously setup radio resource or channel. In some examples, the same radio resource or channel may be used. The transmitter 620 may transmit the slave node authentication information to the master node through the different radio resource or channel. Also, the receiver 610 may receive master node authentication information through the different radio resource or channel.

The master node determines whether the slave node 600 has received a packet including the master node authentication information through the different radio resource or channel. In the event the master node determines the packet has been lost, the master node may terminate a connection with the slave node and may reset up a radio resource or channel.

Technical matters made above with reference to FIGS. 1 through 5 may be applicable to technical matters of FIG. 6 and thus, further descriptions will be omitted.

Figure 7:
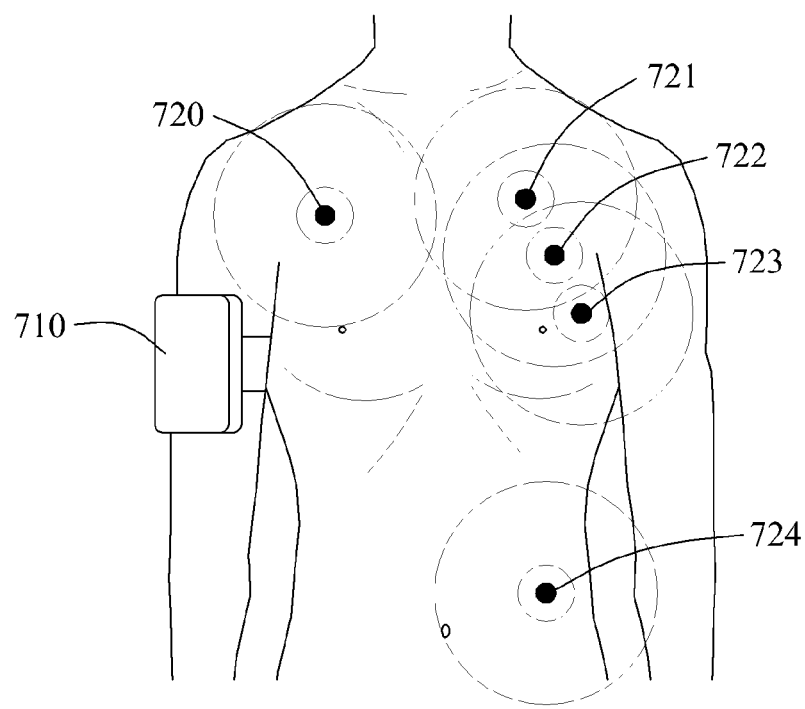
FIG. 7 is a diagram illustrating an example of a wireless body area network (WBAN) including a master node and a slave node.

FIG. 7 is a diagram illustrating an example of a wireless body area network (WBAN) including a master node 710 and slave nodes 720, 721, 722, 723, and 724.

In the WBAN, the master node 710 operates the WBAN by transmitting a beacon for a power control, a time synchronization, and a medium access of the WBAN. The master node 710 may also be referred to as a hub node. Alternatively, the master node 710 may be a coordinator or an access point based on a type of a network. The master node 710 may be a mobile terminal, for example, a smartphone and a personal digital assistant (PDA). The master node 710 may control the WBAN and may be configured to communicate via a WBAN communication protocol. Also, the master node 710 may be configured to connect to an Internet network or a cellular network.

The slave nodes 720, 721, 722, 723, and 724 measure biosignals of a user, and transfer the measured biosignals to the master node 710. Each of the sensor nodes 720, 721, 722, 723, and 724 may be a sensor node. For example, each of the slave nodes 720, 721, 722, 723, and 724 may be a wearable device. Each of the slave nodes 720, 721, 722, 723, and 724 may encrypt a biosignal using a master key. Each of the slave nodes 720, 721, 722, 723, and 724 may transfer the encrypted biosignal to the master node 710.

Technical matters described with reference to FIGS. 1 through 6 may be applicable to technical matters of FIG. 7 and thus, further descriptions will be omitted.

The apparatuses, units, modules, devices, and other components illustrated in FIGS. 1B, 2, 6, and 7 that perform the operations described herein with respect to FIGS. 1A-7 are implemented by hardware components. Examples of hardware components include controllers, sensors, generators, drivers, and any other electronic components known to one of ordinary skill in the art. In one example, the hardware components are implemented by one or more processors or computers. A processor or computer is implemented by one or more processing elements, such as an array of logic gates, a controller and an arithmetic logic unit, a digital signal processor, a microcomputer, a programmable logic controller, a field-programmable gate array, a programmable logic array, a microprocessor, or any other device or combination of devices known to one of ordinary skill in the art that is capable of responding to and executing instructions in a defined manner to achieve a desired result. In one example, a processor or computer includes, or is connected to, one or more memories storing instructions or software that are executed by the processor or computer. Hardware components implemented by a processor or computer execute instructions or software, such as an operating system (OS) and one or more software applications that run on the OS, to perform the operations described herein with respect to FIGS. 1A-7. The hardware components also access, manipulate, process, create, and store data in response to execution of the instructions or software. For simplicity, the singular term "processor" or "computer" may be used in the description of the examples described herein, but in other examples multiple processors or computers are used, or a processor or computer includes multiple processing elements, or multiple types of processing elements, or both. In one example, a hardware component includes multiple processors, and in another example, a hardware component includes a processor and a controller. A hardware component has any one or more of different processing configurations, examples of which include a single processor, independent processors, parallel processors, single-instruction single-data (SISD) multiprocessing, single-instruction multiple-data (SIMD)

multiprocessing, multiple-instruction single-data (MISD) multiprocessing, and multiple-instruction multiple-data (MIMD) multiprocessing.

The methods illustrated in FIGS. 3-5 that perform the operations described herein with respect to FIGS. 1A-7 are performed by a processor or a computer as described above executing instructions or software to perform the operations described herein.

Instructions or software to control a processor or computer to implement the hardware components and perform the methods as described above are written as computer programs, code segments, instructions or any combination thereof, for individually or collectively instructing or configuring the processor or computer to operate as a machine or special-purpose computer to perform the operations performed by the hardware components and the methods as described above. In one example, the instructions or software include machine code that is directly executed by the processor or computer, such as machine code produced by a compiler. In another example, the instructions or software include higher-level code that is executed by the processor or computer using an interpreter. Programmers of ordinary skill in the art can readily write the instructions or software based on the block diagrams and the flow charts illustrated in the drawings and the corresponding descriptions in the specification, which disclose algorithms for performing the operations performed by the hardware components and the methods as described above.

The instructions or software to control a processor or computer to implement the hardware components and perform the methods as described above, and any associated data, data files, and data structures, are recorded, stored, or fixed in or on one or more non-transitory computer-readable storage media. Examples of a non-transitory computer-readable storage medium include read-only memory (ROM), random-access memory (RAM), flash memory, CD-ROMs, CD-Rs, CD+Rs, CD-RWs, CD+RWs, DVD-ROMs, DVD-Rs, DVD+Rs, DVD-RWs, DVD+RWs, DVD-RAMs, BD-ROMs, BD-Rs, BD-R LTHs, BD-REs, magnetic tapes, floppy disks, magneto-optical data storage devices, optical data storage devices, hard disks, solid-state disks, and any device known to one of ordinary skill in the art that is capable of storing the instructions or software and any associated data, data files, and data structures in a non-transitory manner and providing the instructions or software and any associated data, data files, and data structures to a processor or computer so that the processor or computer can execute the instructions. In one example, the instructions or software and any associated data, data files, and data structures are distributed over network-coupled computer systems so that the instructions and software and any associated data, data files, and data structures are stored, accessed, and executed in a distributed fashion by the processor or computer.

While this disclosure includes specific examples, it will be apparent to one of ordinary skill in the art that various changes in form and details may be made in these examples without departing from the spirit and scope of the claims and their equivalents. The examples described herein are to be considered in a descriptive sense only, and not for purposes of limitation. Descriptions of features or aspects in each example are to be considered as being applicable to similar features or aspects in other examples. Suitable results may be achieved if the described techniques are performed in a different order, and/or if components in a described system, architecture, device, or circuit are combined in a different manner, and/or replaced or supplemented by other components or their equivalents. Therefore, the scope of the disclosure is defined not by the detailed description, but by the claims and their equivalents, and all variations within the scope of the claims and their equivalents are to be construed as being included in the disclosure.

What is claimed is:

1. A master node comprising:
    a scheduler configured to transmit, to a slave node, first resource reservation information, and to allocate a first radio resource corresponding to the first resource reservation information;
    an exchanger configured to transmit first security information of the master node to the slave node and receive first security information of the slave node using the allocated first radio resource; and
    a controller configured to determine whether the master node successfully receives the first security information of the slave node and the slave node successfully receives the first security information of the master node, and, based on the determination, generate second security information using the first security information of the slave node and the first security information of the master node,
    wherein the exchanger is further configured to transmit the generated second security information to the slave node and receive second security information of the slave node using second radio resource, and
    wherein the scheduler is further configured to transmit second resource reservation information to the slave node in response to the controller having determined that the master node does not successfully receive the first security information of the slave node or the slave node does not successfully receive the first security information of the master node, and to allocate a third radio resource corresponding to the second resource reservation information.

2. The master node of claim 1, wherein the first security information of the master node comprises either one or both of a public key and a random value corresponding to the master node, and the first security information of the slave node comprises either one or both of a public key and a random value corresponding to the slave node.

3. The master node of claim 2, wherein the controller is configured to determine whether either one or both of the first security information of the master node and the first security information of the slave node has been lost.

4. The master node of claim 2, wherein the scheduler is configured to transmit second resource information to the slave node in response to the controller having determined that the first security information of the master node and the first security information of the slave node were successfully transferred, and to allocate the second radio resource, and
    the second security information of the slave node is generated at the slave node based on the first security information of the master node and the first security information of the slave node.

5. The master node of claim 4, wherein the controller is configured to determine whether the second security information of the master node and the second security information of the slave node has been lost.

6. The master node of claim 4, wherein the first security information of the master node and the first security information of the slave node are included in a first packet group,
    the second security information of the master node and the second security information of the slave node are included in a second packet group, and the scheduler is configured to set up a first dedicated channel for exchanging a plurality of packets included in the first packet group, and to set up a second dedicated channel for exchanging a plurality of packets included in the second packet group.

7. The master node of claim 6, wherein the controller is configured to terminate a connection of the first dedicated channel in response to the controller having determined that a packet comprised in the first packet group has been lost.

8. The master node of claim 1, further comprising:
a master key generator configured to generate a master key used to encrypt data transmitted and received between the master node and the slave node in response to the controller having determined that the second security information of the master node and the second security information of the slave node were successfully transferred.

9. A master node comprising:
a scheduler associated with a link layer; and
a security manager configured to transfer first and second security information to the scheduler,
wherein the security manager is further configured to request the scheduler to allocate a first radio resource for exchanging the first security information with the slave node and a second radio resource for exchanging the second security information with the slave node, and
the link layer is configured to transmit the first security information to the slave node using the allocated first radio resource, and in response to the first security information being successfully exchanged, transmit the second security information to the slave node using the allocated second radio resource.

10. The master node of claim 9, wherein the scheduler is configured to manage the first and second radio resources.

11. The master node of claim 9, further comprising:
a controller configured to determine a presence or an absence of an error in a packet for the exchanging of the first and second security information, and to control the scheduler to allocate another radio resource in response to the presence of the error.

12. The master node of claim 11, wherein the controller is configured to cancel the packet for the exchanging in response to the presence of the error.

13. An operation method of a master node, the method comprising:
transmitting, to a slave node, first resource reservation information;
allocating a first radio resource corresponding to the first resource reservation information;
transmitting first security information of the master node to the slave node and receiving first security information of the slave node;
determining whether the master node successfully receives the first security information of the slave node and the slave node successfully receives the first security information of the master node;
based on the determination, generating second security information using the first security information of the slave node and the first security information of the master node;
transmitting the generated second security information to the slave node and receive second security information of the slave node using second radio resource; and
transmitting second resource reservation information to the slave node in response to having determined that the master node does not successfully receive the first security information of the slave node or the slave node does not successfully receive the first security information of the master nod, and allocating a third radio resource corresponding to the second resource reservation information.

14. The method of claim 13, wherein the first security information of the master node comprises either one or both of a public key and a random key corresponding to the master node, and the first security information of the slave node comprises either one or both of a public key and a random key corresponding to the slave node.

15. The method of claim 14, wherein the determining comprises determining whether either one or both of the first security information of the master node and the first security information of the slave node has been lost.

16. The method of claim 14, further comprises:
transmitting second resource reservation information to the slave node in response to a determination that the first security information of the master node and the first security information of the slave node were successfully transferred,
wherein the second security information of the slave node is generated at the slave node based on the first security information of the master node and the first security information of the slave node.

17. The method of claim 16, further comprises determining whether the second security information of the master node and the second security information of the slave node has been lost.

18. The method of claim 13, further comprising:
transmitting, to the slave node, additional resource reservation information, in response to having determined that the first security information of the master node and the first security information of the slave node were successfully transferred; and
allocating the other resource corresponding to the additional resource reservation information.

* * * * *